United States Patent [19]

Yon et al.

[11] Patent Number: 5,177,298
[45] Date of Patent: Jan. 5, 1993

[54] LIQUID PHASE ADSORPTION PROCESS

[75] Inventors: Carmen M. Yon, Carmel; Joe Quock, Hopewell Juction, both of N.Y.; Wim P. Reel, Emblem, Belgium; Henry Rastelli, New Fairfield, Conn.

[73] Assignee: UOP, Des Plaines, Ill.

[21] Appl. No.: 717,296

[22] Filed: Jun. 18, 1991

[51] Int. Cl.$^5$ .................. C07C 7/12; B01J 20/34
[52] U.S. Cl. .................. 585/824; 585/820; 585/823; 585/826; 502/34
[58] Field of Search ........... 585/820, 823, 824, 826; 502/34

[56] References Cited

U.S. PATENT DOCUMENTS

| | | | |
|---|---|---|---|
| 2,720,547 | 10/1955 | Wolff et al. | 260/614 |
| 3,726,942 | 4/1973 | Louder | 260/683.61 |
| 4,118,425 | 10/1978 | Herbstman | 260/614 A |
| 4,219,678 | 8/1980 | Obenaus et al. | 568/697 |
| 4,252,541 | 2/1981 | Herbstman | 44/56 |
| 4,329,516 | 5/1982 | Al-Muddarris | 568/697 |
| 4,734,199 | 3/1988 | Nagji et al. | 210/674 |
| 4,740,631 | 4/1988 | Nagji et al. | 568/697 |
| 4,814,517 | 3/1989 | Trubac | 568/697 |
| 4,816,607 | 3/1989 | Vora et al. | 568/697 |
| 4,830,734 | 5/1989 | Nagji et al. | 585/826 |
| 4,935,399 | 6/1990 | Blackburn et al. | 502/34 |

OTHER PUBLICATIONS

Chemical and Engineering News, p. 35, Jun. 25, 1979.
Paper presented at the American Institute of Chemical Engineers, 85th National Meeting, Jun. 4–8. 1978 by F. Obenaus et al., pp. 271–275.

*Primary Examiner*—Anthony Mc Farlane
*Assistant Examiner*—Nhat Phan
*Attorney, Agent, or Firm*—Thomas K. McBride; Tolomei John G.; Richard P. Silverman

[57] ABSTRACT

A process for the regeneration of oxygenate containing adsorbents uses regenerant streams such as LPG and isomerate products for the desorption of oxygenate compounds. The process discloses arrangements for the integration of regenerant treatment into the adsorption scheme and for the enhancement of the isomerate product. The integrated flowscheme can be used to remove sulfur and water from contaminated regenerants or to deliver the oxygenates into the gasoline pool.

16 Claims, 2 Drawing Sheets

LIQUID PHASE ADSORPTION PROCESS

BACKGROUND OF THE INVENTION

1. Field of the Invention

The present invention relates in general to adsorption separation processes. More particularly, this invention relates to fixed bed adsorption systems comprising multiple beds, and the integration of typical refinery streams as regenerant streams.

2. Description of the Prior Art

A variety of arrangements are known for adsorption separation processes. One type as practiced in the prior art, is shown in U.S. Pat. Nos. 4,734,199 and 4,740,631 and discloses as many as six distinct steps, namely:

(a) adsorption of one or more components from a feedstock mixture;
(b) draining the bed of unprocessed feedstock;
(c) regeneration of the bed using a heated purge fluid;
(d) cooling down the newly regenerated bed in preparation for a new adsorption step by passage into the bed of a cooling medium;
(e) draining the cooling medium from the cooled bed; and
(f) filling the void space of the cooled bed with fresh feedstock.

These steps are more fully characterized below:

Adsorption step (a): During this step the liquid phase feedstock containing the impurities to be removed is passed through a vessel containing a suitable particulate adsorbent such as a zeolitic molecular sieve. As the feed passes through the adsorbent bed the impurities (sorbates) are selectively held up by the adsorbent. The feed, now containing significantly less impurity, leaves the adsorption vessel as product. The adsorption step is continued for a fixed time interval or until the impurity levels in the product exceed specifications. At this time the feed is directed to another adsorption vessel of the system, this vessel having been previously regenerated.

Feedstock Drain Step (b): During this drain step, the feedstock remaining in the void space of the vessel at the end of the adsorption step (a) is drained by gravity or pumped out and recycled to feed. If the vessel is drained slowly then the time required for draining will constitute a significant portion of the overall cycle time. If the vessel is drained quickly then the additional flow rate due to material combining with the feed must be considered when sizing the sorbent requirement. In either case, the elimination of the drain step would be of considerable advantage in a liquid phase sorption system.

Regeneration Heat Step (d): After draining step (b), a heated regeneration medium is passed through the adsorbent bed. As the adsorbent is heated it releases the previously sorbed sorbate. The sorbate passes into the regeneration heating medium and is carried out of the system by the latter. The heating step is continued until the bulk of the impurities have been carried out of the adsorption vessel. Regeneration heating is usually carried out with a regenerating medium differing from both product and feedstock.

Regeneration-Cool Step (d): During this step a cooling medium is passed through the hot adsorption vessel to carry out the sensible heat remaining in the adsorption vessel at the end of the regeneration heat step. The cooling is continued until the bulk of sensible heat is carried out of the sorption vessel. In many instances cooling is carried out with a medium other than the feedstock. It is customary to drain this medium before proceeding to the fill step. This adds another step to the overall process cycle.

Cooling Medium Drain Step (e) the step in which the cooling medium remaining in the adsorbent bed void space at the end of Regeneration Cool Step (d) is removed from the bed either by gravity flow or by pumping.

Void Space Filling Step (f): During the fill step, either product or feedstock is used to fill the void spaces in the adsorption vessel before returning the vessel back into service. This is necessary since failure to do so will result in two phase flow and vapor lock. In large volume sorption vessels the time required for filling the vessel can be substantial especially since often the rate at which feed or product is available is often limited. Upon completion of the fill step the sorption vessel is ready to be put back into the sorption step.

In the above processes the regenerant fluid, although heated, remains in the liquid phase requiring a drain step at the end of the regeneration-cool step. It is preferred to operate the process with the regenerant in the vapor phase during the desorption step. Operation of the regeneration cycle in the vapor phase permits the processing of feedstocks with relatively small quantities of oxygen-containing compounds. The objective of the present invention is to remove trace amounts of oxygenates such as methanol, methyl tertiary butyl ether (MTBE), dimethyl ether (DME), tertiary butyl alcohol (TBA) and water from a reactor effluent stream wherein the concentration of each of these oxygenates ranges from 20 to 2000 ppm wt. and the total amount of oxygenates in the stream ranges from 1000 to 2500 ppm wt. The operation of the regeneration in the vapor phase further permits a pressure assisted drain step to drain the liquid feedstock from the bed at the beginning of the regeneration cycle. A small amount of vaporized regenerant less than 20% of the total is permitted to enter the effluent end of the adsorber bed, forcing the feedstock from the bed. This operation significantly shortens the drain step and provides some initial bed heating. When all of the feedstock has drained from the bed, the full flow of vapor regenerant can be passed over the adsorbent to desorb the oxygen-containing hydrocarbons. The vapor is recirculated and heated until the bed reaches the required temperature for desorption, typically this ranges from 200°-300° C. At the conclusion of the desorption step, the bed must be cooled to adsorption conditions, typically ranging from 25°-50° C. Typically, the bed is cooled by introducing a liquid regenerant which may be the feedstock, the product, or a separate fluid. The initial passing of liquid through the bed in an upflow manner often results in a degree of vaporization of the regenerant liquid which provides further cooling.

The ideal regenerant is a dry, sulfur-free gas. However, in a petroleum refinery there are very few sources of dry gases with a minimum of impurities such as sulfur compounds which would be suitable for this application. Impurities such as water, sulfur and heavy hydrocarbons may contaminate the adsorbent and reduce its effectiveness or shorten its useful life.

Typically, this process used lighter molecular species or the same molecular species as the product for the regenerant. It was generally believed, by those skilled in the art, that regenerant streams containing hydrocarbons that are heavier than the product would interfere with the operation of the adsorbent. Normal butane was often used for the regenerant. When this butane could be blended into gasoline, there were some gasoline octane benefits. However, current U.S. Environmental Protection Agency requirements to reduce the vapor pressure of gasoline has restricted this use for butane.

One of the major applications for this technology is in the manufacture of a high octane motor gasoline component such as methyl tertiary alkyl ethers in these processing arrangements as described in U.S. Pat. No. 4,816,607. The production of ethers by the reaction of an isoolefin with an alcohol is well known and is practiced commercially. This highly selective reaction is also used to remove olefins, especially isobutylene, from mixed hydrocarbon streams such as the $C_4$ streams produced in stream cracking plants which produce ethylene. Increased attention has been focused on ether production due to the rapidly increasing demand for lead-free octane boosters for gasoline such as MTBE. A detailed description of the processes, including the catalysts, processing conditions and product recovery, for the production of MTBE from isobutylene and methanol are provided in U.S. Pat. Nos. 2,720,547 and 4,219,678 and in an article at page 35 of the Jun. 25, 1979 edition of *Chemical and Engineering News*. The preferred process is described in a paper presented at the American Institute of Chemical Engineers 85th National Meeting on Jun. 4-8, 1978 by F. Obenaus, et al. Descriptions of integrated process, including those which utilize butane isomerization are found in U.S. Pat. Nos. 3,726,942, 4,118,425, 4,252,541, and 4,329,516.

In U.S. Pat. No. 4,814,517 to Trubac a dual or compound adsorption bed containing silica gel and zeolite 13X is employed to first selectively remove methanol and then selectively remove dimethylether from an etherification effluent within a process scheme for the production of methyl tertiary butyl ether, MTBE. The adsorber system is regenerated in the liquid phase with normal butane as the regenerant.

BRIEF SUMMARY OF THE INVENTION

The invention provides a method of regenerating solid adsorbents used to remove oxygen-containing compounds from a process stream of an integrated etherification process. The method comprises contacting the usual sorbent with a high temperature stream comprising a hydrocarbon present in a typical petroleum refinery where the availability of suitable regenerant streams are limited.

This invention provides a solution to the problem of finding a suitable regenerant and, where beneficial, retaining the octane quality of the oxygenates for use in the gasoline pool through the use of specific vaporized regenerants. Regenerants for this invention are usually first treated by adsorption to remove sulfur compounds. In such cases, a portion of the treated desorbent is then used to desorb oxygenate compounds from an oxygenate adsorption system while another portion of the regenerant is used to desorb sulfur compounds from the sulfur adsorption zone. Saturate $C_3$ and $C_4$ hydrocarbons, commonly known as LPG and the isomerized $C_5$–$C_6$ fraction of a crude oil stream are used as the regenerants of this invention.

It has also been discovered that the isomerized $C_5$–$C_6$ fraction, normally called isomerate, has good gasoline blending characteristics, even though, it represents a higher molecular weight material than the feedstock processed herein. Using isomerate as a vapor regenerant permits the process to be used to effectively remove oxygenates with surprising results and still retain the benefits of recovering oxygenates for use in gasoline blending. Thus, using the isomerate as a regeneration stream has special advantages even when it is used without sulfur removal steps.

In a more complete aspect of the present invention, a LPG stream, which typically contains impurities comprising sulfur compounds and water, is employed as a regenerant to desorb oxygen-containing compounds, or oxygenates from a solid adsorbent wherein sulfur compounds and water are deleterious to the function of the solid adsorbent. A first adsorption system is positioned upstream of the adsorbent for rejecting oxygen-containing compounds. The first adsorption system selectively removes the impurities in the LPG, a portion of the treated sweet LPG is used to desorb the oxygen-containing compounds in the oxygenate removal section and a portion of the sweet LPG is used to desorb the first adsorption system returning the sulfur compounds and water to produce a sour LPG by-product stream. Both a sweet and a sour LPG by-product may be subsequently used for fuel in the refinery.

In another aspect of the invention, a hydrocarbon stream comprising isomerized $C_5$–$C_6$ paraffins is vaporized and used as a regenerant to desorb oxygen-containing hydrocarbons from solid adsorbent. Upon condensation, the isomerate combined with the rejected oxygen-containing hydrocarbons are passed to the gasoline blending pool wherein the surprising benefit is that the isomerate now has a higher research octane and the refinery has retained the higher value use of the oxygen-containing compounds.

DETAILED DESCRIPTION OF THE INVENTION

Figure 1:
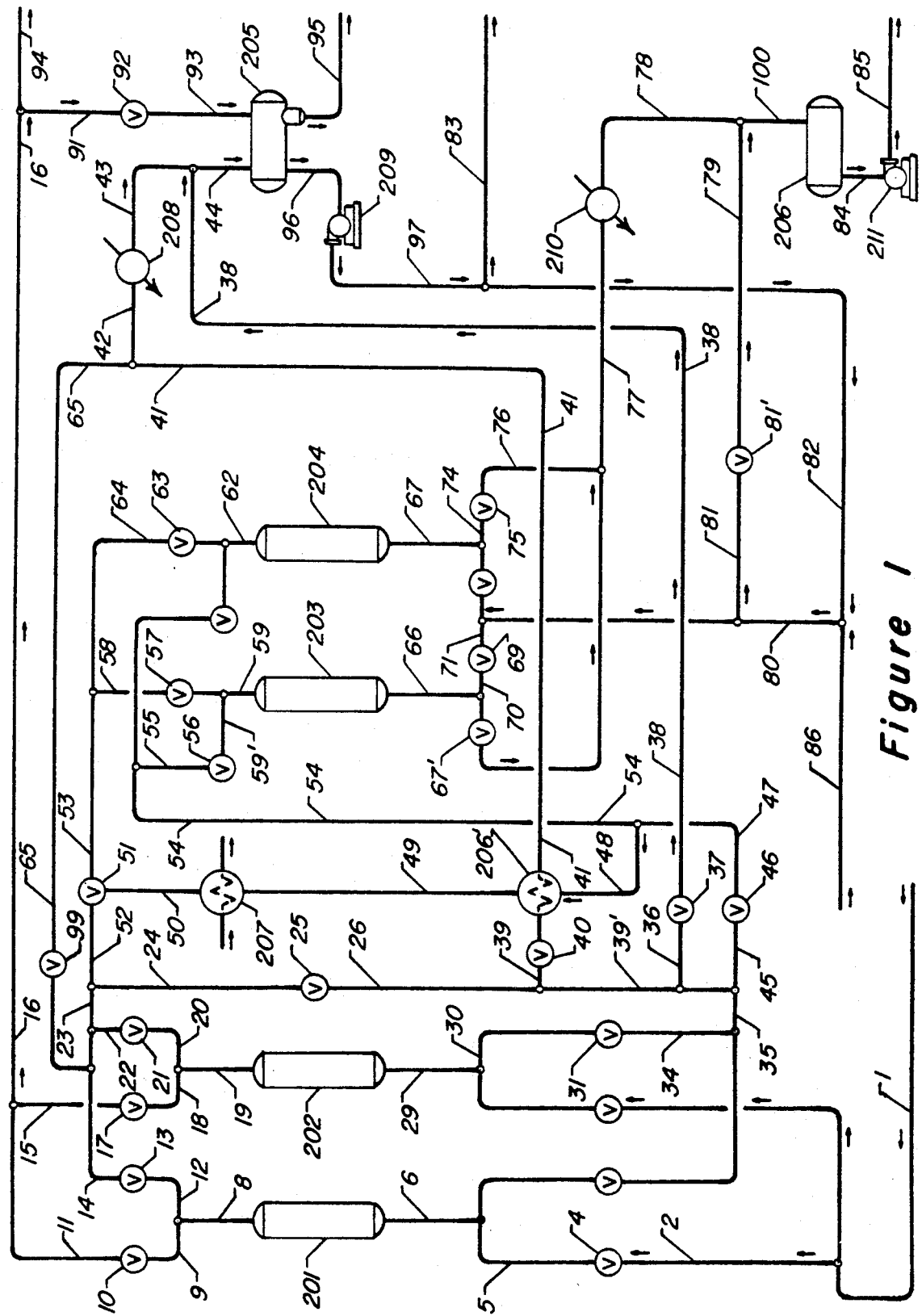
FIG. 1 is a schematic flow diagram for an adsorption system comprising a sulfur and water removal section and oxygen-containing hydrocarbon rejection section.

The adsorption process of the present invention is carried out in the liquid phase and the desorption process of the current invention is carried out in the vapor phase.

The feedstocks suitably treated by the present process are not a narrowly critical factor, it being the principal properties of such feedstocks that are normally in the liquid phase under the pressure conditions which can reasonably be imposed on the adsorption system. Also the feedstocks must contain a constituent, preferably a minor constituent, which is selectively adsorbed by the sorbent employed. Such feedstocks include mixtures of hydrocarbons where the sorptive selectivity is based on molecular size, degree of unsaturation or degree of volatility. The selectively adsorbed impurity can be a non-hydrocarbon such as water, alcohols, sulfides, nitrogen containing compounds and organometallics. The illustration of the invention below is concerned with such a process.

The particular adsorbent involved is also not a critical feature. Any of the commonly used solid adsorbents such as activated alumina, silica gel or zeolitic molecular sieves can be employed. It has been found that a sodium zeolite X is well suited to this application. Of the zeolite adsorbents, particularly zeolite 5A, zeolite 13X and zeolite D are preferred. More preferably zeolite 13X offers particular advantages in adsorbing trace amounts of oxygenates.

The temperature and pressure conditions to be utilized are in the main dependent upon the feedstocks being treated and the adsorbent employed. In general, the temperature at which the adsorption purification step is carried out is, when possible, at near ambient temperature typically ranging from 25°–50° C. since lower temperatures favor adsorption but higher or lower temperatures can be used. Pressure conditions are chosen to maintain the feedstocks and cooling streams in the liquid phase and to move the fluids through the system at the desired rates; typically pressures range from 150 to 200 psia. The degree to which the regeneration purge streams are elevated in temperature typically ranging from 200°–300° C. is also largely dependent upon the particular adsorbate being removed from the sorbent and also the particular sorbent employed. The selection of all of these operating parameters is well within the routine skill of those familiar with the adsorption purification art.

As one of its primary functions, the process of this invention rejects oxygenates from a stream of unreacted hydrocarbons and oxygen-containing compounds. In the case of methyl tertiary butyl ether (MTBE) production, these compounds are MTBE, methanol and by-products including dimethyl ether and tertiary butyl alcohol. Other schemes (4,575,565) disclose the means for removing these oxygen-containing compounds to supply a treated process stream substantially free of the oxygen-containing compounds, but are silent on their disposition.

This process is especially suited for using refinery streams that are not generally suited as regenerant fluids for oxygenate adsorption zones. Regenerant streams that pass through the oxygenate adsorption zone must be low in sulfur compounds and olefinic and aromatic hydrocarbons. Thus, the typical high sulfur content of an LPG stream makes it unsuitable as a desorbent. Most isomerate streams have a low enough concentration of sulfur and unsaturated hydrocarbons to make them suitable adsorbents. However, this low sulfur concentration is usually the result of some prior treatment steps. Thus, this invention can be incorporated into such schemes to provide the necessary treatment of the isomerate for upstream processes as well as oxygenate desorption. Moreover, some isomerate streams may still have a sulfur concentration that is unsuitable for sustained used as a desorbent. In such cases this invention has the advantage of allowing only a part of the isomerate stream to be treated for use as an adsorbent.

In most cases the oxygen-containing compounds remain in the regenerant fluid. If the fluid is a natural gas, or other light hydrocarbon stream, the oxygen-containing compounds are burned for fuel. If the regenerant fluid is, however, a gasoline blending component which does not contain unacceptable concentrations free of impurities such as olefins, sulfur compounds and water, the rejected oxygen-containing compounds can be combined with this material to provide additional octane benefits.

Looking particularly at LPG, in a typical refinery this stream may be produced from a variety of processes, but the LPG often contains total sulfur, typically ranging from 100 to 150 ppm wt., and water which could be detrimental to the operation of the adsorbent.

It is preferred that the regenerant for this process be dry and contain less than 1 ppm wt. total sulfur. Thus, where needed, this invention provides a separate adsorption section for the drying and selective removal of sulfur compounds from the regenerant stream such that in the adsorption mode the regenerant stream will have a suitable composition. Again, in the case of LPG, the normally wet, sour stream is first passed to a drying and sulfur removal adsorber to produce a dry, sweet LPG which is, heated and passed to the adsorbent bed of the oxygenate removal unit during desorption. In addition, a portion of the dry, sweet LPG is returned to a different drying and sulfur removal adsorber undergoing desorption. Thus, the drying and sulfur adsorption system and the adsorption system for rejecting oxygen-containing compounds share the dry, sweet regeneration stream wherein the impurities which are potentially harmful to the second adsorption system were removed.

The practice of this invention with a wet, sour LPG stream to provide the regenerant stream for an oxygenate adsorption system is illustrated with reference to FIG. 1. The feedstock being treated in this illustrative process is the effluent from an etherification reaction to make a methyl tertiary alkyl ether following the removal of the ether and the removal of unreacted $C_4$-minus aliphatic monocyclic alcohols. The alcohols are chosen from methanol, ethanol, primary and secondary propanol, the various butanols, and other alcohols. Methanol and ethanol are particularly preferred. The majority of the description of the invention is presented in terms of the reaction of isobutene with methanol since these are the preferred feed materials and this is the commercially predominant reaction. However, it is not intended to thereby lessen the scope of the inventive concept.

The other component of the etherification reaction is a $C_4$–$C_6$ cyclic hydrocarbon or a single carbon number mixture of isomeric hydrocarbons. The hydrocarbon may, therefore, be substantially pure normal butane, normal pentane or a mixture of the corresponding isomeric and normal hydrocarbons. The preferred hydrocarbon is a mixture of isobutane and normal butane such as is available from several sources in a petroleum refinery, or as available as field butanes. This variety of possible hydrocarbon materials allows the production of a wide variety of ethers other than the preferred MTBE including methyl tertiary amyl ether, ethyl tertiary aryl ether and ethyl tertiary butyl ether.

The effluent from the etherification reaction is passed to a separation zone wherein the MTBE is separated from the effluent whereby the MTBE is taken as the bottoms product and the separation zone effluent is taken overhead to a methanol removal section. In the methanol removal section, the remaining effluent is typically water washed or passed through an adsorption process to remove the unreacted methanol which is returned to the etherification reaction. The methanol depleted separation zone effluent has the following typical amounts of oxygenates:

| | |
|---|---|
| Dimethylether | 200–750 ppm wt. |
| Water | 500 ppm wt. |
| Methanol | 20 ppm wt. |
| TBA | 10 ppm wt. |
| MTBE | 10 ppm wt. | and is hereinafter referred to as the feedstock. In the operation of this illustrative process, the overall cycle requires 960 minutes; i.e., the time interval required from the beginning of an adsorption-purification step in one of the adsorption beds until the beginning of the next adsorption-purification step in the same bed.

The feedstock is passed into the process via lines 1 and 2 to valve 4 and from valve 4 through lines 5 and 6 to oxygenate adsorber bed 201 containing an adsorbent such as activated alumina and/or crystalline zeolitic molecular sieves having the capacity to adsorb trace amounts of oxygenates comprising methanol, MTBE, TBA, DME and water. The preferred adsorbent for this process is a commercially available zeolite X molecular sieve known as zeolite 13X. The temperature within adsorbent bed 201 is at an initial temperature of about 38° C. Immediately prior to introduction of the feedstock into bed 201, the bed contains one bed void volume of the liquid regeneration cool-down medium as a result of the immediately prior regeneration of bed 201. This regeneration cool-down medium is a portion of the dry, sweet LPG. The bed regeneration procedure is described hereinafter with respect to oxygenate adsorbent bed 202.

The upflow of feedstock into bed 201 continues for a total of 480 minutes, during which time oxygenates are adsorbed selectively and retained in the bed. For the first 15 minutes, the effluent from bed 201 is principally the regeneration cool-down medium which filled the bed immediately prior to the beginning of the feedstock flow therein. Over this 15 minute period, the regeneration medium effluent passes up from bed 201 through lines 8 and 12, valve 13, lines 14, 23 and 24, valve 25, lines 26, 39', 35 and 34, valve 31 and lines 30 and 29 to enter the bottom of bed 202, until the void volume of bed 202 is filled with regenerant from bed 201. Thereafter, for the remaining 465 minutes of the aforesaid 480 minute flow period of feedstock into bed 201, the effluent flowing through lines 8 and 9, valve 10 and out of the system through lines 11, 16 and 94, is $C_4$ hydrocarbon product containing less than 10 wt. ppm of oxygenates. This stream will usually have an oxygenate concentration of between 1 and 10 wt. ppm and is suitable for subsequent processing in downstream refining processes such as butane isomerization, alkylation and dehydrogenation.

At the beginning of the passage of the feedstock into bed 201, bed 202 has completed the adsorption-purification step except that there remains in the bed void space about one bed void volume of feedstock. Flow of feedstock into bed 202 has been terminated at the point where the adsorbent therein retains sufficient capacity to adsorb the amount of oxygenates present in the void space feedstock. In conventional practice, this bed volume of feedstock would be drained from the bed using a separate draining step before the beginning of the regeneration steps. In the present process, however, the drain step is avoided by using the bed volume of the void space regeneration cool-down medium which is the effluent from bed 201 at this time to force the bed volume of feedstock in bed 202 upward over the unspent adsorbent therein and out of bed 202 via lines 19 and 18, valve 17 and lines 15, 16 and 94. If it is necessary to avoid contamination of the product with $C_3$'s in the regenerant, this stream is returned to separator 205. This by-pass time is 9.5 minutes, starting 10 minutes into the displacement time. This effluent moves from bed 202 through lines 19 and 18, valve 17 and lines 15, 16 and 91 to valve 92 and on to separator 205 via line 93.

During the displacement step, an LPG treater containing adsorbers 203 and 204 is on standby. At the conclusion of the displacement step, bed 202 and bed 204 must be drained of liquid regenerant in preparation for the vapor heating and desorption step. The draining is usually accomplished by a pressure assisted drain step which is effected by the introduction of a small portion of regenerant as superheated vapor. If the entire regenerant were vaporized, the resulting vapor could create high gas velocities. The LPG regenerant enters the process via line 86. A small fraction, less than 20%, of regeneration liquid entering via line 86, passes on via lines 80 and 71 to valve 69 and lines 70 and 66 to the bottom of bed 203 which is still hot from a prior regeneration. The remainder of the regenerant is by-passed via line 81 through valve 81' and lines 79 and 100 to separator 206. As the regenerant cools the bed 203, it is vaporized, passing out of the bed 203 via lines 59 and 59' to valve 56 and on to superheater 207 via lines 55, 54, 48 and 49. During this phase there is no hot spent regeneration vapor through exchanger 206'. The regeneration liquid fed to bed 203 may include at least a portion of liquid regenerant recycle from separator 205 via line 96, pump 209, line 97 and line 82 which joins the fresh regenerant flow in line 80.

The superheated regeneration vapor enters the top of bed 202 via line 50, through valve 51 to lines 52, 23, 22, 20 and 19 and through valve 21. A small fraction of the superheated vapor is also routed to bed 204 via lines 53, 64 and 62 and valve 63.

The superheated regenerant vapor heated to a temperature of between 200°-240° C., enters bed 202 and forces the liquid from the adsorbent bed to separator 205 via lines 29, 30, 34, 35, 36, 38 and 44, passing through valves 31 and 37. The superheated regenerant entering bed 204 via lines 53 and 64, valve 63 and line 62 forces the fluid drained from bed 204 into separator 206 via lines 67, 74, 76, 77, 78, and 100, passing through valve 75 and condenser 210. Once all of the liquid is drained in this manner from beds 202 and 204 the full regeneration flow can be routed through lines 86, 80, 71 and valve 69 to lines 70 and 66 to bed 203. The heating phase begins at this point.

During the heating step, hot dry, sweet regenerant is required to desorb the oxygenates removed from the feedstock and desorb the sulfur compounds removed from the regenerant liquid. Regenerant liquid comprising fresh regenerant in line 86 and recycled sweet spent regenerant from line 82 are passed to the bottom of adsorber 203 via lines 80 and 71 to valve 69 and from that point passed through lines 70 and 66. Here the regenerant liquid initially will be heated in bed 203 and exit the bed as a vapor via lines 59 and valve 56. This vapor is passed to lines 55 and 48 where it encounters cross-exchanger 206'. At the start of the heating phase there will be no heat recovery in cross exchanger 206, however, at the end of the heating phase, a major portion of the vaporization heat will be recovered. From cross exchanger 206', the regenerant is passed via line 49 to superheater 207 wherein the temperature of the regenerant is raised to about 240° C. The superheated regenerant vapor is passed via line 50 to valve 51 which splits the superheated vapor to provide a major portion to desorb oxygenates from bed 202 and a minor portion to desorb sulfur compounds and water in bed 204. To desorb oxygenates in bed 202 the superheated vapor is passed via lines 52 and 22 to valve 21 and through lines 20 and 19 to bed 202. The spent sweet regenerant flows through lines 29 and 30 and valve 31 and is passed to valve 40 via lines 34, 35, 39' and 39. From valve 40 the hot sweet spent regenerant vapor is passed to cross exchanger 206 for heat recovery to provide the partial heating of sweet liquid regenerant. The cooler sweet spent regenerant stream is passed through lines 41 and 42 to condenser 208. At condenser 208, the sweet spent regenerant is condensed and sent to separator 205 via lines 43 and 44. In separator 205 the condensed sweet spent regenerant forms a hydrocarbon phase and an aqueous phase. Each phase contains a portion of the desorbed oxygenates. Oxygenates recovered in the aqueous phase are removed from the process via line 95 and oxygenates in the hydrocarbon phase are removed via line 83, downstream of pump 209 and lines 96 and 97. This material may be used as sweet LPG by product elsewhere in the refinery as it flows from separator 205 to pump 209, via line 96 and from line 97 to line 83. A portion of the sweet spent regenerant is passed via line 82 to a point where it joins line 86 to form line 80.

The minor portion of the superheated regeneration vapor is conducted via lines 53 and 64 to valve 63 and line 62 to the top of adsorber 204, wherein the adsorbed sulfur compounds and water from the previous cycle are desorbed. The spent regenerant from this desorption is sour since it contains sulfur and must be kept apart from the remainder of the regenerant. Therefore, the sour regenerant leaving bed 204 is conducted via lines 67 and 74 through valve 75 and lines 76 and 77 to condenser 210. Condenser 210 condenses the sour regenerant vapor which is passed to separator 208 via lines 78 and 100. This sour LPG is withdrawn as a liquid by product via line 84 and raised to the required pressure by pump 211 to distribute the sour LPG to other uses in the refinery via line 85.

Following the heating step, the oxygenate bed 202 will undergo a cool down step, while the sulfur removal bed 204 will be isolated in a hot standby mode for the next cycle. In the cool/fill step, the sweet liquid regenerant moves from line 54 to line 47 and valve 46 and continues through lines 45, 35 and 34, valve 31 and is passed to the bottom of bed 202 via lines 30 and 29. As the liquid regenerant cools and fills bed 202, hot vapor will exit the top of the bed via lines 19 and 20, through valve 21 and lines 22 and 23, and further is passed via line 98 through valve 99 to lines 65 and 42. The hot vapor is condensed in exchanger 208 and collected in separator 205 via lines 43 and 44. A portion of this liquid will be recycled via lines 96 to pump 209 and lines 97 and 82 to provide sufficient regenerant for the cooling of the oxygenate adsorber bed. This cool/fill step continues for the duration of this segment of the cycle, returning bed 202 to an adsorption temperature of about 38° C. and leaving the bed 202 filled with regenerant. The process then continues in a similar manner with beds 202 and 204 in the adsorption mode while beds 201 and 203 undergo regeneration.

As will be apparent from the foregoing, a significant attribute of the present process is the ease with which the product flow rates can be maintained constant. This is due to the fact that one of the absorber beds in either the removal of oxygenates or the removal of sulfur and water from LPG is always in operation producing a product. The production of product is maintained on a continuous basis during the drain and fill operations and during the heating and cooling steps. Other advantages will be obvious to those skilled in the art, particularly when the peculiarities of specific feedstocks and regeneration media are taken into account.

One group of components in a typical refinery which produces unleaded gasoline is an isomerized $C_5$-$C_6$ stream or isomerate. This material is sometimes suited as a regenerant because it is often free of sulfur compounds, olefins and aromatic compounds like benzenes. Sulfur compounds and benzene were found to interfere with the selectivity of the adsorbent to adsorb the oxygen-containing compounds. Olefinic compounds often result in the formation of coke on the adsorbent during the desorption process. Many of the oxygen-containing compounds have a research octane number of 115 to 120. When even small amounts of these materials are added to an isomerized $C_5$-$C_6$ stream, research octane of 83-91, there will be a significant benefit to the motor octane of the combination and hence a benefit to the motor gasoline pool.

Figure 2:
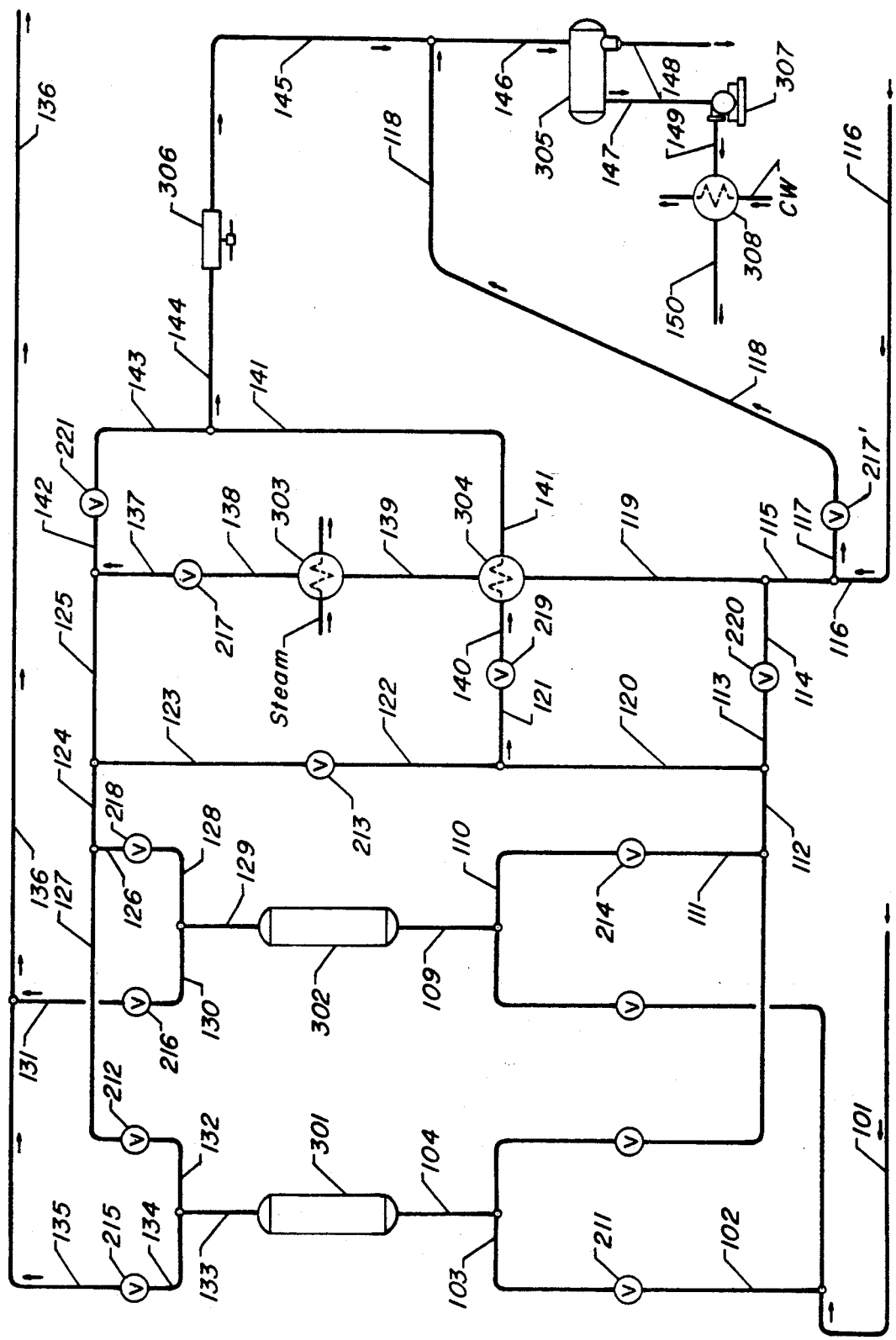
FIG. 2 is a schematic flow diagram of an adsorption system comprising two adsorbent beds with a $C_5$–$C_6$ isomerate regenerant.

It has also surprisingly been found that the heavy hydrocarbons do not appreciably interfere with the effectiveness of the adsorbent when an isomerate is used as a regenerant stream. Therefore, in the case of low sulfur isomerates, it is possible to use such streams without the integrated sulfur removal step. FIG. 2 illustrates such a process arrangement where a low sulfur isomerate is used as the regenerant stream for the same feedstock described above in conjunction with the sulfur containing regenerant stream.

With respect to FIG. 2, the feedstock enters the system through lines 101 and 102 in the liquid phase at a temperature of about 38° C. (100° F.) and under a pressure of about 150 psia. The feedstock passes through valve 211 and lines 103 and 104 to adsorbent bed 301 containing zeolitic molecular sieve adsorbent having capacity to adsorb trace quantities of oxygenates comprising methanol, MTBE, tertiary butyl alcohol (TBA), dimethyl ether (DME), and water. A preferred adsorbent for this purpose is the commerical zeolite widely known as zeolite X.

The temperature within adsorbent bed 301 is at an initial temperature of about 38° C. Immediately prior to introduction of the feedstock into bed 301, the bed contains one bed volume of the liquid regeneration cool-down medium as a result of the immediately prior regeneration of bed 301. This regeneration cool-down medium is a portion of the $C_5$-$C_6$ isomerate in the liquid phase.

The bed regeneration procedure is described hereinafter with respect to adsorbent bed 302. The upflow of feedstock into bed 301 continues for a total of 480 minutes, during which time oxygenates are adsorbed selectively and retained in the bed. For the first 15 minutes, the effluent from bed 301 is principally the regeneration cool-down medium which filled the bed immediately prior to the beginning of the feedstock flow thereunto. Over this 15 minute period, the regeneration medium effluent passes up from bed 301 through lines 133 and 132, valve 212, lines 127, 124 and 123, valve 213, lines 122, 120, 112 and 111, valve 214 and lines 110 and 109 to enter the bottom of bed 302 until the void volume of the bed is filled with regenerant from bed 301. Thereafter for the remaining 465 minutes of the aforesaid 480 minute flow period and an additional 15 minutes during the next displacement step, product flows from bed 301 through lines 133 and 134, valve 215 and out of the system through lines 135 and 136. The product comprises $C_4$ hydrocarbons containing less than 10 wt. ppm of oxygenates and typically oxygenates in a range of 1 to 10 wt. ppm. This stream is suitable for subsequent processing in downstream refinery processes such as alkylation and dehydrogenation.

At the beginning of the passage of the feedstock into bed 301, bed 302 has completed the adsorption-purification step except that there remains in the bed void space about one bed volume of feedstock. Flow of feedstock into bed 302 has been terminated at the point where the adsorbent therein retains sufficient capacity to adsorb the amount of oxygenates present in the void space feedstock. In conventional practice, this bed volume of feedstock would be drained from the bed using a separate draining step before the beginning of the regeneration steps. In the present process, however, the drain step is avoided by using the bed volume of the void space regeneration cool-down medium which is the effluent from bed 301 at this time to force the bed volume of feedstock in bed 302 upward over the unspent adsorbent therein and out of bed 302 as product effluent free of oxygenates. This effluent moves from bed 302 through lines 129 and 130, valve 216 and lines 131 and 136 as $C_4$ hydrocarbon product. This displacement stage requires 15 minutes. At the conclusion of the displacement step, bed 302 must be drained of liquid regenerant in preparation for the vapor heating and desorption step. The fresh liquid regenerant enters via line 116. This drain step is affected by the introduction of a small portion less than 20% of the total regenerant as superheated vapor at the top of bed 302. Excess regenerant by-passes a heater via line 117, valve 217 and lines 118 and 146 to the regenerant separator 305. The remainder of the regenerant enters lines 115 and 119, passes through heat exchanger 304, line 139, line 138, and steam superheater 303 to valve 217'. From line 137 the superheated regenerant flows through lines 125, 124 and 126, valve 218 and flows downward through bed 302 from lines 128 and 129. The liquid regenerant in the void space of bed 302 is forced out of the bed via lines 109 and 110, through valve 214, lines 111 and 112, lines 120 and 121, through valve 210, line 140 through the heat exchanger 304 and lines 141, lines 144, condenser 306, lines 145 and 146 to phase separator 305. This pressure assisted drain step requires 15 minutes to remove the fluid from the bed 302. Once the bed is free of fluid, the heating step begins by heating the fresh regenerant from lines 116, 115 and 119 through heat exchanger 304 and further passing the heated regenerant via line 139 to superheater 303 wherein the regenerant is heated to a temperature in the range of 200°-300° C. (400°-550°), more preferably in a range of 200°-240° C. The superheated regenerant vapor is passed from line 137, through lines 125 and 126, valve 218 and through lines 128 and 129 downward through bed 302. In passing the superheated regenerant vapor through bed 302, the regeneration medium heats the adsorbent and oxygenates are desorbed and carried out of the bed with the hot spent regenerant. The hot spent regenerant vapor is passed from bed 302 through lines 109 and 110, through valve 214 and along lines 111, 112, 120 and 121 to valve 219. From valve 210, the hot spent regenerant vapor exchanges heat in heat exchanger 304 with fresh regenerant and moves through lines 141 and 144 to condenser 306 and on to separator 305 via lines 145 and 146. The hydrocarbon phase of the condensed spent regenerant comprising regenerant and adsorbed oxygenates is removed from the separator 305 via line 147 to pump 307 to cooler 308 via line 149 which reduces the temperature of the condensed spent regenerant and conducts the material to storage or to gasoline blending via line 150. The aqueous phase of line 148 separated in separator 305 contains water and some dissolved oxygenates which may be returned to the MTBE complex for recovery of any methanol. The heating step continues for a total of 260 minutes.

At the conclusion of the heating step, bed 302 begins the cool and fill step wherein the bed 302 is filled from the bottom with liquid regenerant and cooled to adsorption conditions. Fresh liquid regenerant is passed from lines 116 and 115 through line 114 and valve 220 and lines 113, 112 and 111 to valve 214. The regenerant enters bed 302 through lines 110 and 109. As the liquid regenerant enters the hot adsorbent, a portion of the regenerant material vaporizes, providing some sensible cooling. The regenerant passes through the top of bed 302 via lines 129 and 128 and valve 218. The regenerant is then conducted via lines 126, 124, 125 and 142 to valve 221 to condenser 306 via line 143 and 144 where it is condensed. The condensed regenerant is passed to separator 305 via lines 145 and 146. This cooling process continues for 190 minutes, returning the bed 302 to a temperature of about 38° C. and filling bed 302 with regenerant.

As will be immediately apparent to those skilled in the art from the foregoing description, that the pressure assisted drain step used between the displacement step and the heat step significantly reduces the overall cycle time over a gravity assisted drain step or through the use of a mechanical pump as required in the prior known processes. Thus, the cycle times take advantage of this significant reduction.

We claim:

1. A process for the continuous liquid phase adsorption of oxygenates from an oxygenate-containing liquid hydrocarbon feedstock with a regenerant stream comprising hydrocarbons and at least 10 wt. ppm sulfur compounds, said process comprising:
   (a) passing the feedstock to a first of at least two fixed adsorbent beds containing a solid adsorbent having selectivity for the adsorption of oxygenates and recovering from the first bed a product having a lower concentration of oxygenates than the liquid hydrocarbon feedstock;
   (b) terminating the passage of said feedstock into the first adsorbent bed and passing said feedstock to a second adsorbent bed said second adsorbent bed initially containing a sweet regenerant in the liquid phase;
   (c) passing said feedstock into said second adsorbent bed, displacing sweet regenerant in liquid phase from said second adsorbent bed and passing the displaced regenerant to said first adsorbent bed while recovering treated product from said first adsorbent bed;
   (d) passing an untreated liquid regenerant to a third adsorbent bed containing a solid adsorbent for the removal of sulfur compounds and recovering a sweet regenerant;
   (e) heating at least a portion of said sweet regenerant;
   (f) passing a portion of said sweet regenerant in vapor phase to said first adsorbent bed to desorb oxygenates from the adsorbent, and recovering a spent sweet regenerant vapor containing oxygenates;
   (g) passing a portion of said sweet regenerant in vapor phase to a fourth adsorbent bed containing a solid adsorbent for the removal of sulfur compounds to desorb sulfur compounds from said fourth adsorbent bed and recovering a spent, sour regenerant vapor;

(h) cooling and filling said first adsorbent bed by passing sweet regenerant in the liquid phase to said first adsorbent bed and recovering sweet regenerant;

(i) terminating the flow of regenerant to the fourth adsorbent bed and terminating the flow of regenerant to the first adsorbent bed and reversing the process cycle of steps (b) to (h) for said first and second, and said third and fourth adsorbent beds.

2. The process of claim 1 wherein the adsorbent for the first and second adsorbent beds is an activated alumina or a zeolitic molecular sieve.

3. The process of claim 1 wherein the adsorbent for the first and second adsorbent beds is zeolite 13X.

4. The process of claim 1 wherein the adsorbent for the third and fourth adsorbent beds is a zeolitic molecular sieve.

5. The process of claim 1 wherein the adsorbent for the third and fourth adsorbent beds is zeolite 13X.

6. The process of claim 1 wherein the temperature of the first and second adsorbent beds is between 25° and 50° C. during the adsorption of oxygenates.

7. The process of claim 1 wherein said sweet regenerant is superheated.

8. The process of claim 7 wherein the temperature of the superheated sweet regenerant is at least 240° C.

9. The process of claim 1 step (c) wherein at least a portion of the treated productt is diverted to a first separator for at least a portion of the time during the displacement of sweet regenerant from the second adsorbent bed to avoid contamination of the finished product with the regenerant.

10. The process of claim 9 wherein the displaced sweet regenerant is drained from the first adsorbent bed, and sweet regenerant is superheated and passed to the top of the first adsorber bed to force the displaced sweet regenerant from said first adsorbent bed and said sweet regenerant is recovered in the first separator.

11. The process of claim 9 step (e) wherein a portion of said first dry, sweet regenerant is superheated and passed to the top of the first adsorbent bed to force the displaced liquid regenerant from said first adsorbent bed.

12. The process of claim 1 wherein said regenerant stream comprises a sour liquified petroleum gas (LPG) stream.

13. The process of claim 1 step (d) wherein the feedstock from the first adsorbent bed is drained by passing a portion of the sweet regenerant as a superheated sweet very regenerant vapor to the top of the first adsorbent bed to force the liquid feedstock from the bed.

14. The process of claim 13 wherein the portion of superheated sweet regenerant vapor and is less than 20% of the sweet regenerant.

15. The process of claim 1 wherein the temperature of the adsorber during the adsorption of oxygenates ranges from 25°–50° C.

16. A process for the continuous liquid phase adsorption of trace amounts of oxygenates from an oxygenate containing liquid hydrocarbon feedstock with a regenerant stream comprising a wet liquified petroleum gas (LPG) stream having at least 10 wt. ppm sulfur compounds, said process comprising:

(a) passing the feedstock to a first of at least two fixed adsorbent beds containing a solid adsorbent having selectivity for the adsorption of oxygenates and recovering from the first bed a product having a lower concentration of oxygenates than the liquid hydrocarbon feedstock;

(b) terminating the passage of said feedstock into the first adsorbent bed said second adsorbent bed initially containing a sweet regenerant in liquid phase;

(c) passing said feedstock into said second adsorbent bed, displacing sweet liquid regenerant in liquid phase from the second adsorbent bed, passing the displaced regenerant to said first adsorbent bed while recovering treated product from said first adsorbent bed for the duration of the regenerant displacement;

(d) passing a portion of an untreated liquid regenerant stream to a third adsorbent bed containing a solid adsorbent for the removal of sulfur compounds and water and recovering a first dry, sweet regenerant;

(e) draining the displaced liquid regenerant from said first adsorbent bed and recovering a first liquid regenerant stream in a first separator;

(f) passing at least a portion of said untreated liquid regenerant stream and at least a portion of said first liquid regenerant stream from said first separator to said third adsorbent bed, recovering a second dry, sweet regenerant and superheating said second dry, sweet regenerant;

(g) passing a major portion of the superheated dry sweet regenerant to said first adsorbent bed to desorb oxygenates from the adsorbent and recovering a spent sweet regenerant vapor containing oxygenates;

(h) passing a minor portion of the superheated dry sweet regenerant to a fourth adsorbent bed containing a solid adsorbent for the removal of sulfur compounds to desorb sulfur compounds and water from said fourth adsorbent bed and recovering a spent sour regenerant vapor;

(i) condensing said spent sweet regenerant vapor, passing the condenser vapor to said first separator and recovering a first hydrocarbon phase comprising sweet regenerant and oxygenates and an aqueous phase comprising oxygenates;

(j) recycling a portion of said first hydrocarbon phase to provide additional regenerant;

(k) cooling and filling said first adsorbent bed by passing dry, sweet regenerant in the liquid phase to the bottom of said first adsorbent bed and from said first adsorbent bed to said first separator;

(l) condensing the spent sour regenerant vapor of step (h), passing the condensed sour liquid to a second condensor and recovering the condensed sour liquid as a by-product;

(m) terminating the flow of regenerant to the fourth adsorbent bed and terminating the flow of regenerant to the first adsorbent bed and reversing the process cycle of steps (b) to (l) for said first and second, and said third and fourth adsorbent beds.

* * * * *